(12) United States Patent
Hsueh

(10) Patent No.: US 10,653,459 B2
(45) Date of Patent: May 19, 2020

(54) SPINAL FIXATION AIMING APPARATUS

(71) Applicant: Shao-Kang Hsueh, New Taipei (TW)

(72) Inventor: Shao-Kang Hsueh, New Taipei (TW)

( * ) Notice: Subject to any disclaimer, the term of this patent is extended or adjusted under 35 U.S.C. 154(b) by 0 days.

(21) Appl. No.: 15/928,111

(22) Filed: Mar. 22, 2018

(65) Prior Publication Data

US 2018/0206891 A1    Jul. 26, 2018

Related U.S. Application Data

(63) Continuation-in-part of application No. 15/098,319, filed on Apr. 14, 2016, now abandoned.

(51) Int. Cl.
| | |
|---|---|
| A61B 17/70 | (2006.01) |
| A61B 17/17 | (2006.01) |
| A61B 17/16 | (2006.01) |
| A61B 17/00 | (2006.01) |
| A61B 90/30 | (2016.01) |
| A61B 90/50 | (2016.01) |
| A61B 90/11 | (2016.01) |

(52) U.S. Cl.
CPC ...... *A61B 17/7083* (2013.01); *A61B 17/1757* (2013.01); *A61B 17/7076* (2013.01); *A61B 17/16* (2013.01); *A61B 17/1655* (2013.01); *A61B 90/11* (2016.02); *A61B 90/30* (2016.02); *A61B 90/50* (2016.02); *A61B 2017/00477* (2013.01); *A61B 2017/00907* (2013.01)

(58) Field of Classification Search
CPC ..... A61B 17/7076; A61B 90/50; A61B 90/11; A61B 90/30
See application file for complete search history.

(56) References Cited

U.S. PATENT DOCUMENTS

| | | | | |
|---|---|---|---|---|
| 4,719,907 A | * | 1/1988 | Banko | A61B 17/1721 606/65 |
| 4,723,544 A | * | 2/1988 | Moore | A61B 17/3403 604/116 |
| 5,571,072 A | * | 11/1996 | Kronner | F16M 11/08 248/279.1 |
| 6,605,088 B1 | * | 8/2003 | St. Onge | A61F 5/05 606/54 |
| 7,736,371 B2 | * | 6/2010 | Schoepp | A61B 17/3403 604/104 |
| 2006/0084900 A1 | * | 4/2006 | Schule | A61B 90/57 602/36 |

* cited by examiner

*Primary Examiner* — Lynnsy M Summitt
*Assistant Examiner* — Tara Rose E Carter
(74) *Attorney, Agent, or Firm* — Leong C. Lei

(57) ABSTRACT

A spinal fixation aiming apparatus includes a spinal fixation aiming device, a first adjustment unit, a second adjustment unit, and an extendible/retractable bar. The spinal fixation aiming device includes an arc guide rail, an arc slide unit, and a tool holder that is movable to and selectively fixed at a predetermined position. The arc guide rail, the arc slide unit, and the tool holder are each made of a light-transmitting materials. To use, the extendible/retractable bar is attached to an operation table and adjustment is made with the first adjustment unit, the second adjustment unit, and the extendible/retractable bar for setting a position of the spinal fixation aiming device to an angle and a height according to the patient. Further, according to the need of the surgical operation, a collaborative operation of the arc guide rail and the arc slide unit can be conducted for angular adjustment.

11 Claims, 3 Drawing Sheets

SPINAL FIXATION AIMING APPARATUS

CROSS-REFERENCE TO RELATED APPLICATION

This is a continuation-in-part of co-pending U.S. patent application Ser. No. 15/098,319 filed on Apr. 14, 2016.

TECHNICAL FIELD OF THE INVENTION

The present invention relates generally to a novel spinal fixation aiming apparatus, and more particularly to one for use in spine related surgeries.

DESCRIPTION OF THE PRIOR ART

The modern spinal fixation surgeries are generally conducted by incising the back of a patient along a central line and cutting off supraspinous ligaments. The muscles next to the spine are pushed aside by periosteal elevators to a nailing site for fixation and the muscles are held in such a position by being pulled to two sides by hooks. This leads to tendons that are attached to the spine being cut off and damage of the muscles and tendons around the spine would inevitably occur. The following disadvantage would happen:

(1) When the surgery is completed and the muscles are stitched back, the muscles and tendons that are around the spine cannot be placed back and held at the site before the surgery and this would severely damage the muscles of the surgery patient.

(2) There is an excessively wide dead space and this would lead to epidural fibrosis after the surgery, making the result of operation poor.

(3) The spine would become unstable after the surgery due to supraspinous ligaments, vertebral spine, and interspinous ligaments of the patient all being cut off To overcome the drawbacks of the conventional spinal fixation surgeries, minimal invasion spinal fixation surgeries that have a minimal incision and the minimum extent of damage of muscular tissues have been proposed. Two commonly used processes have been adopted for minimal invasion spinal fixation surgeries. The first one is that fixation is conducted by way of percutaneous pedicle and implantation and the second one is using an expansion sleeve to conduct fixation with visual observation. However, there are still drawbacks as follows:

(I) Fixation by way of percutaneous pedicle:

(1) Excessive light transmission would occur during the process of the surgery and may cause damage to the vision of the surgeons and the patient.

(2) For most bone fractures of high location lumbar vertebra or thoracic vertebra, retrogressive low waist detachment or instability of spine would result, leading to high difficulty of surgery and being not used often.

(3) The implants and devices used in the surgery are specially designed for percutaneous surgeries and thus, the cost for developing such surgery devices is expensive.

(II) Fixation by way of expansion sleeve:

(1) Although direct visual observation is possible for surgeons, the fixation nailing site is often full of densely distributed blood vessels related to wide circulation, making it often to cause massive bleeding during the operation. In addition, the surgery wound at the nailing site is generally deep, leading to undesired influence on the eyesight of the surgeon and thus difficulty of the surgical operation.

(2) The expansion sleeve, the implant, and the surgery devices fused in the surgical operation may often hit each other and thus cause interference with the performance of the surgical operation.

(3) The expansion sleeve used in the surgery is not light transmittable and may block the light of a surgical lighting device during the performance of the surgery.

SUMMARY OF THE INVENTION

The primary objective of the present invention is such that in use of the present invention, an extendible/retractable bar is attached to an operation table and adjustment is made with a first adjustment unit, a second adjustment unit, and the extendible/retractable bar for setting a position of a spinal fixation aiming device to an angle and a height according to the patient. Further, according to the need of the surgical operation, a collaborative operation of an arc guide rail and an arc slide unit can be conducted for angular adjustment so that the tool holder can keep corresponding to a spinal fixation nailing site of the patient for any angle thereby providing an effect of easy operation and accurate aiming.

To achieve the above objective, the present invention provides a spinal fixation aiming apparatus, which comprises: a spinal fixation aiming device, a first adjustment unit, a second adjustment unit, and an extendible/retractable bar. The spinal fixation aiming device comprises an arc guide rail, an arc slide unit that is movably coupled to the arc guide rail, and a tool holder that is mounted to the arc slide unit. Two ends of the arc guide rail are each formed with a mounting hole. The tool holder is movable to and selectively fixed at a predetermined location. The arc guide rail, the arc slide unit, and the tool holder are each formed of a light-transmitting material. The first adjustment unit is coupled to one of the mounting holes of the arc guide rail for adjusting inclination and height of the spinal fixation aiming device. The second adjustment unit is coupled to the first adjustment unit for adjustably setting the spinal fixation aiming device to a first horizontal position or a second horizontal position. The extendible/retractable bar is movably coupled to the second adjustment unit for adjusting a height of the spinal fixation aiming device.

In the spinal fixation aiming apparatus according to the present invention, the arc slide unit comprises a base, guide sections respectively extending from ends of the base, through openings respectively formed in the guide sections and movably coupled to the arc guide rail, and a fixing knob selectively fixing the arc guide rail.

In the spinal fixation aiming apparatus according to the present invention, the tool holder comprises a coupling section, slide covers respectively arranged at two sides of the coupling section and respectively engageable with and coupled to the guide sections, an internally threaded section extending through each of the slide covers, and a threading fastener coupled to each of the internally threaded sections.

In the spinal fixation aiming apparatus according to the present invention, the tool holder receives a tool sleeve to position therein.

In the spinal fixation aiming apparatus according to the present invention, the first adjustment unit comprises a mounting section coupled to the second adjustment unit, an angle adjustment seat movably coupled to the mounting section, and a height adjustment seat movably coupled to the angle adjustment seat.

In the spinal fixation aiming apparatus according to the present invention, the angle adjustment seat is coupled to the mounting section by at least one first adjustment knob and the height adjustment seat is coupled to the angle adjustment seat by at least one second adjustment knob.

In the spinal fixation aiming apparatus according to the present invention, the second adjustment unit comprises a first rail movably coupled to the first adjustment unit, an adjustment fixer movably coupled to the first rail, and a second rail movably coupled with the extendible/retractable bar and the adjustment fixer.

In the spinal fixation aiming apparatus according to the present invention, each of the first rail and the second rail has one side that is provided with a toothed section.

In the spinal fixation aiming apparatus according to the present invention, the adjustment fixer comprises a first coupling section fit over and coupled to the first rail, a first fixing member mounted to one side of the first coupling section, a second coupling section fit over and coupled to the second rail, and a second fixing member mounted to one side of the second coupling section.

In the spinal fixation aiming apparatus according to the present invention, the first fixing member is set, in a releasable manner, in engagement with the toothed section of the first rail and the second fixing member is set, in a releasable manner, in engagement with the toothed section of the second rail.

In the spinal fixation aiming apparatus according to the present invention, the extendible/retractable bar has one end that is provided with a pivotal joint section that is movably coupled to the second adjustment unit and the pivotal joint section is provided, on one side thereof, with a pivot fastener.

The foregoing objectives and summary provide only a brief introduction to the present invention. To fully appreciate these and other objects of the present invention as well as the invention itself, all of which will become apparent to those skilled in the art, the following detailed description of the invention and the claims should be read in conjunction with the accompanying drawings. Throughout the specification and drawings identical reference numerals refer to identical or similar parts.

Many other advantages and features of the present invention will become manifest to those versed in the art upon making reference to the detailed description and the accompanying sheets of drawings in which a preferred structural embodiment incorporating the principles of the present invention is shown by way of illustrative example.

DETAILED DESCRIPTION OF THE PREFERRED EMBODIMENTS

The following descriptions are exemplary embodiments only, and are not intended to limit the scope, applicability or configuration of the invention in any way. Rather, the following description provides a convenient illustration for implementing exemplary embodiments of the invention. Various changes to the described embodiments may be made in the function and arrangement of the elements described without departing from the scope of the invention as set forth in the appended claims.

Figure 1:
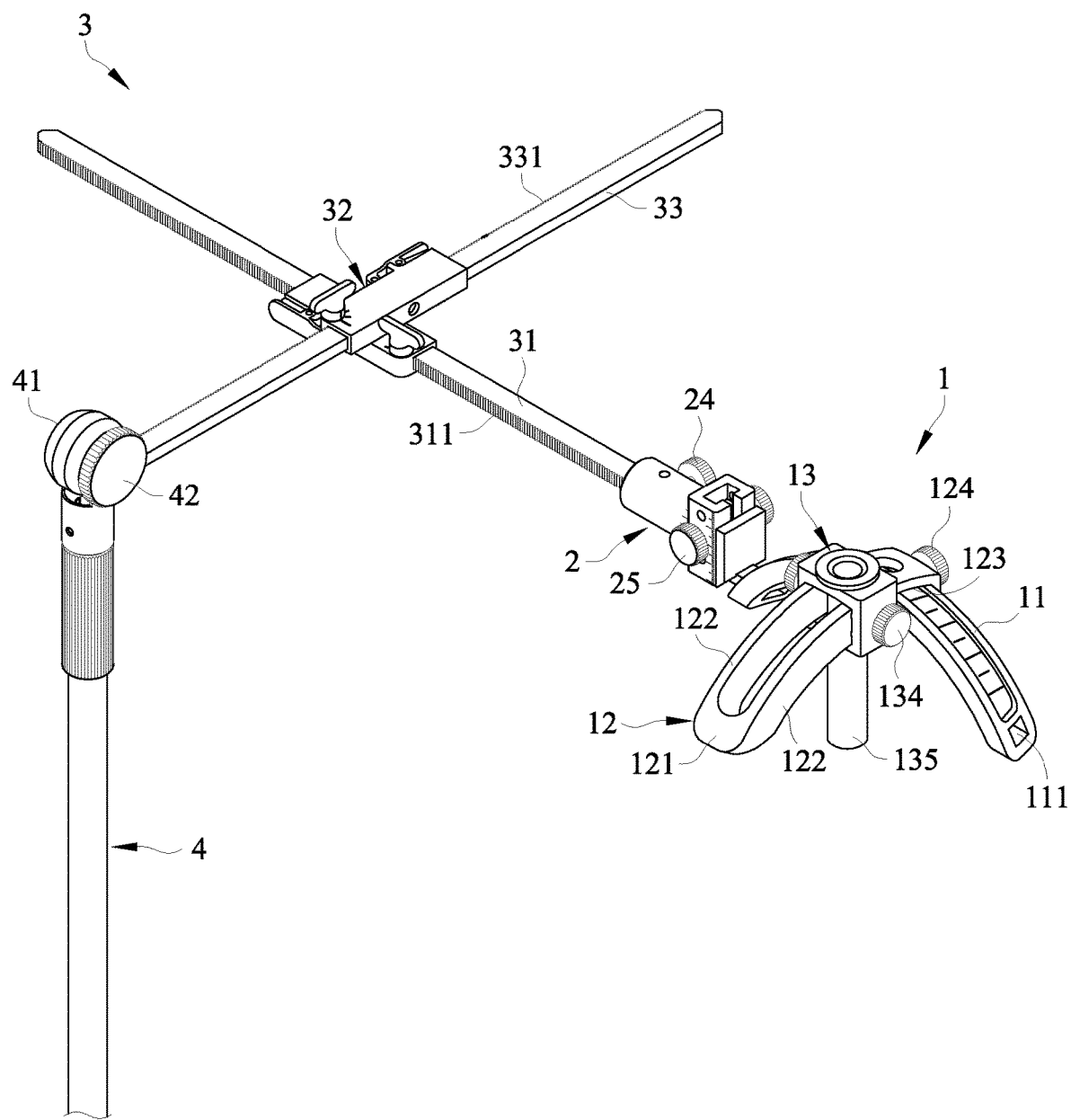
FIG. 1 is a perspective view of the present invention.
Figure 2:
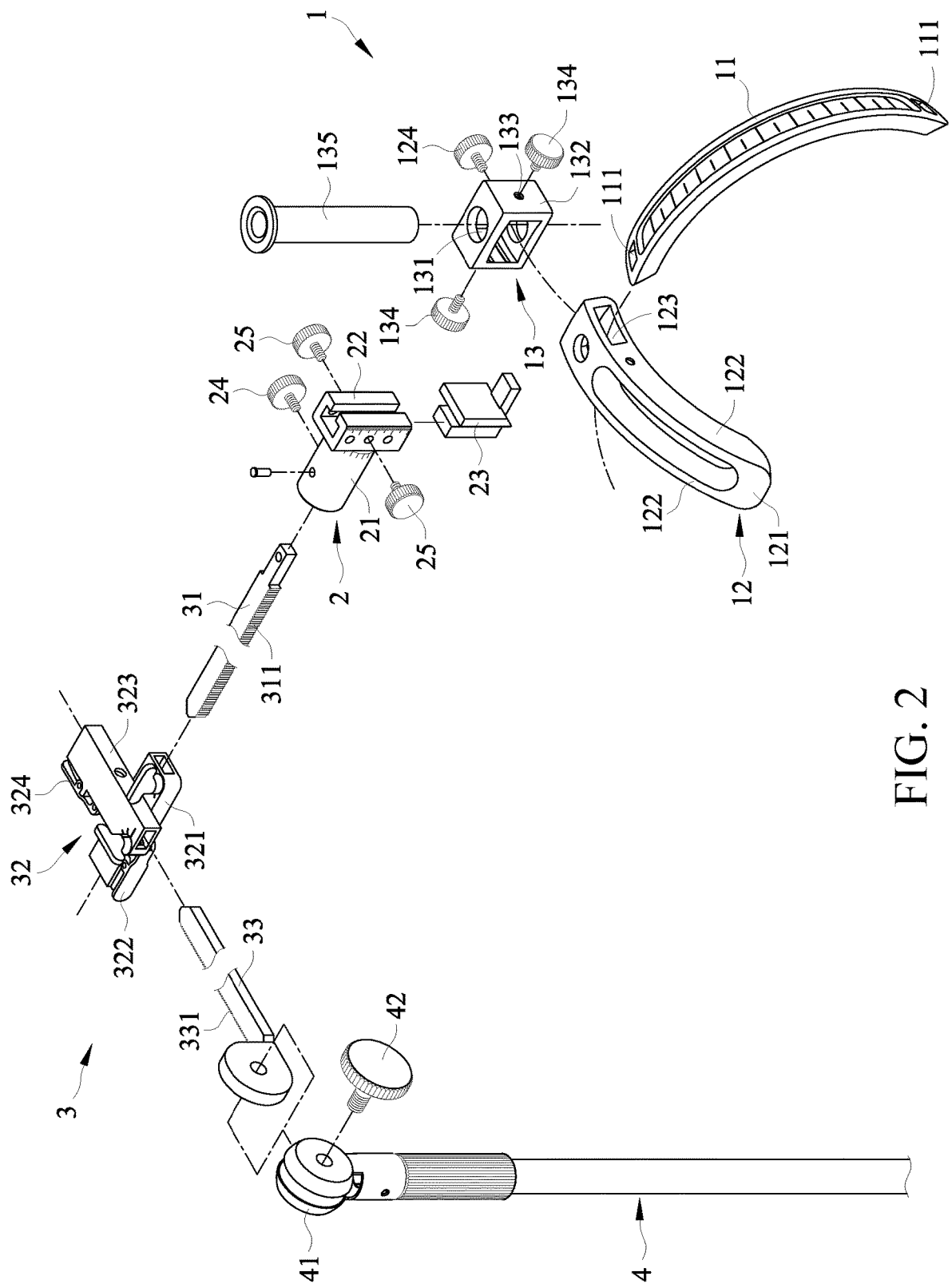
FIG. 2 is an exploded view of the present invention.
Figure 3:
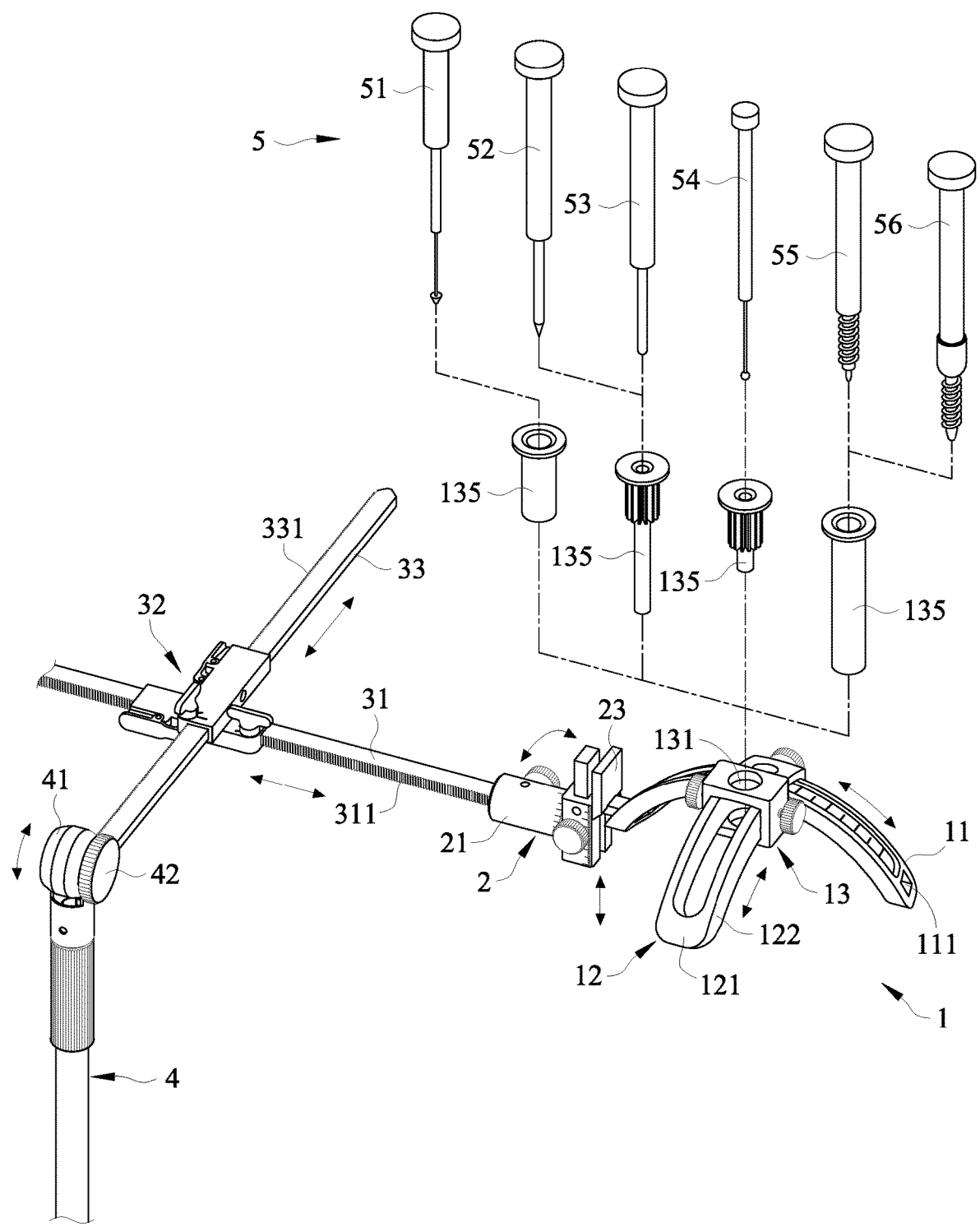
FIG. 3 is a cross-sectional view illustrating an operation condition of the present invention.

Referring to FIGS. 1-3, which are respectively a perspective view and an exploded view of the present invention and a cross-sectional view illustrating an operation of the present invention, as shown in the drawings, the present invention provides a spinal fixation aiming apparatus, which comprises, at least, a spinal fixation aiming device 1, a first adjustment unit 2, a second adjustment unit 3, and a extendible/retractable bar 4.

The spinal fixation aiming device 1 comprises an arc guide rail 11, an arc slide unit 12 that is movably coupled to the arc guide rail 11, and a tool holder 13 that is mounted to the arc slide unit 12. Two ends of the arc guide rail 11 are each formed with a mounting hole 111. The tool holder 13 is movable and is positionable at a desired or predetermined location and releasably fixed at such a location. The arc guide rail 11, the arc slide unit 12, and the tool holder 13 are each formed of a light-transmitting material.

The first adjustment unit 2 is coupled to one of the mounting holes 111 of the arc guide rail 11 for adjusting inclination and height of the spinal fixation aiming device 1.

The second adjustment unit 3 is coupled to the first adjustment unit 2 for adjustably setting the spinal fixation aiming device 1 to a first horizontal position or a second horizontal position.

The extendible/retractable bar 4 is movably coupled to the second adjustment unit 3 for adjusting a height of the spinal fixation aiming device 1. As such, a novel spinal fixation aiming apparatus is constructed with the above-described technical features.

To use the present invention, the extendible/retractable bar 4 is attached to an operation table and adjustment is made with the extendible/retractable bar 4 to set the spinal fixation aiming device 1 to a desired height or vertical location that matches the spine of a patient. According to the site where a surgeon is performing the operation and the location of the spine of the patient, further adjustment is made with the first adjustment unit 2 to set the spinal fixation aiming device 1 to desired inclination and height. Further adjustment is made with the second adjustment unit 3 to set the spinal fixation aiming device 1 to the first horizontal position (which could be a position in an x-axis) or the second horizontal position (which could be a position in a y-axis). With the height and inclination, as well as other positional parameters, of the spinal fixation aiming device 1 being so adjusted, adjustment of angle and position of the arc slide unit 12 with respect to the arc guide rail 11 is then made to suit the need for performance of the operation. The adjustment can be made in such a way that the surgeon may directly apply a force to the arc slide unit 12 for movement thereof, so that the arc slide unit 12 is forcibly moved on the arc guide rail 11 to adjust the angle thereof, in a left-right direction, (the movable range of angle being for example 0-45 degrees), and then a desired position of the tool holder 13 on the arc slide unit 12 is adjusted. To make the adjustment of position, the surgeon may directly apply a force to the tool holder 13 in order to adjust the angle thereof, in a front-rear direction, (the movable range of angle being for example 0-45 degrees). Further, the arc guide rail 11 and the arc slide unit 12 are arranged together to form a spherical surface, so that the tool holder 3 is kept to always aim at a spinal fixation nailing site of the patient (which corresponds to the center of the sphere) for any position to which the arc slide unit 12 or the tool holder 13 is moved and thus, surgical devices can be easily mounted to and supported on the tool holder 13 to allow the surgeon to easily carry out the surgical operation.

Further, the present invention is applicable to minimally invasive surgery that is carried out directly through the skin of the patient. By making the arc guide rail 11, the arc slide unit 12, and the tool holder 13 with light-transmitting materials, observation of the bone where the nailing is to make being blocked or shielded by the skin, muscles, and tendons of the patient can be avoided after the arc guide rail 11, the arc slide unit 12, and the tool holder 13 have been set up and shadow cast by surgical lighting can also be avoided so that the surgeon may gain a better field if vision during the surgical operation. In addition, after the adjustment has been done and the nailing site adjacent to the spine of the patient has been fixed by the surgical device, X-ray photographing may be conducted directly so that the time period in which the surgeon may be exposed to X-ray radiation is significantly shortened and convenience of use during the surgical operation may be achieved.

In an embodiment of the present invention, the arc slide unit 12 comprises a base 121, guide sections 122 respectively extending from ends of the base 121, through openings 123 respectively formed in the guide sections 122 and movably coupled to the arc guide rail 11, and a fixing knob 124 selectively fixing the arc guide rail 11. As such, to made adjustment, the surgeon may directly apply a force to the base 121 (or either one of the guide sections 122) for movement thereof so that the guide sections 122 are made movable, by means of the through opening 123, on and along the arc guide rail 11 to adjustment of angle in a left-right direction. After the adjustment is completed, the position of the arc guide rail 11 can be fixed by means of the fixing knob 124.

In an embodiment of the present invention, the tool holder 13 comprises a coupling section 131, slide covers 132 respectively arranged at two sides of the coupling section 131 and respectively coupled to or engageable with the guide sections 122, an internally threaded section 133 extending through each of the slide covers 132, and a threading fastener 134 coupled to each of the internally threaded sections 133, and in addition, a tool sleeve 135 is mounted to the coupling section 131 of the tool holder 13. As such, to adjust the position of the tool holder 13 on the arc slide unit 12, the surgeon may directly apply a force to one of the threading fasteners 134 to cause the slide covers 132 to respectively move on the guide sections 122 for adjustment of angle in a front-rear direction. After the adjustment is made such that a desired location is reached, forces may be applied to screw the threading fasteners 134 into the internally threaded sections 133, such than an end of each of the threading fasteners 134 abuts the respective one of the guide sections 122 for fixation. Further, the arc guide rail 11 and the arc slide unit 12 are arranged together to form a spherical surface, so that the tool sleeve 135 of the coupling section 131 is kept to always aim at a spinal fixation nailing site of the patient for any position to which the arc slide unit 12 or the tool holder 13 is moved and thus, surgical tools 5 can be easily set in the tool sleeve 135 to allow the surgeon to easily carry out the surgical operation.

In an embodiment of the present invention, the first adjustment unit 2 comprises a mounting section 21 coupled to the second adjustment unit 3, an angle adjustment seat 22 movably coupled to the mounting section 21, and a height adjustment seat 23 movably coupled to the angle adjustment seat 22, wherein the angle adjustment seat 22 is coupled to the mounting section 21 by at least one first adjustment knob 24 and the height adjustment seat 23 is coupled to the angle adjustment seat 22 by at least one second adjustment knob 25. As such, the first adjustment knob 24 can be rotated and loosened to allow for adjustment of the spinal fixation aiming device 1, by means of the angle adjustment seat 22, to a desired inclination and can then be rotated and tightened for fixation; and the second adjustment knob 25 can be rotated and loosened to allow for adjustment of the spinal fixation aiming device 1, by means of the height adjustment seat 23, to a desired height and can then be rotated and tightened for fixation, whereby adjustments of inclination and height can be achieved.

In an embodiment of the present invention, the second adjustment unit 3 comprises a first rail 31 movably coupled to the first adjustment unit 2, an adjustment fixer 32 movably coupled to the first rail 31, and a second rail 33 movably coupled with the extendible/retractable bar 4 and the adjustment fixer 32, wherein one side of each of the first rail 31 and the second rail 33 is provided with a toothed section 311, 331, and the adjustment fixer 32 comprises a first coupling section 321 fit over and coupled to the first rail 31, a first fixing member 322 mounted to one side of the first coupling section 321, a second coupling section 323 fit over and coupled to the second rail 33, and a second fixing member 324 mounted to one side of the second coupling section 323. The first fixing member 322 is set, in a movable and thus releasable manner, in engagement with the toothed section 311 of the first rail 31 and the second fixing member 324 is set, in a movable and the releasable manner, in engagement with the toothed section 331 of the second rail 33. As such, to adjust, through the second adjustment unit 3, the spinal fixation aiming device 1 to a first horizontal position (which is a position in an x-axis) or a second horizontal position (which is a position in a y-axis), the first fixing member 322 or the second fixing member 324 is pressed to disengage from the toothed section 311 of the first rail 31 and the toothed section 331 of the second rail 33 so that the first coupling section 321 and the second coupling section 323 are allowed to move along the first rail 31 and the second rail 33 and once a desired location is reached, the first fixing member 322 and the second fixing member 324 are respectively set in engagement with the toothed section 311 of the first rail 31 and the toothed section 331 of the second rail 33 for fixing the position, whereby the spinal fixation aiming device 1 could be fixed after the adjustment.

In an embodiment of the present invention, one end of the extendible/retractable bar 4 is provided with a pivotal joint section 41 that is movably coupled to the second rail 33 of the second adjustment unit 3. The pivotal joint section 41 is provided, on one side thereof, with a pivot fastener 42. As such, the pivot fastener 42 can be rotated and loosened to allow for adjustment of the second rail 33, by means of the pivotal joint section 41, to a desired height and fixed there by the pivot fastener 42 after the adjustment.

Further, the tool sleeve 135 can be provided in different forms and sizes according to various surgical tools 5 involved. The surgical tools 5 can be for example a positioning device 51, an awl device 52, a puncture device 53, a probe device 54, a tapping device 55, or a screw insertion device 56. The use of each of these surgical tools 5 will be briefly described below:

(1) The positioning device 51: A positioning pin is positionable in the tool sleeve 135 and the spinal fixation aiming device 1 is set at a 0-degree position. When illumination is made with lighting of the surgical lights, positioning can be made through visibility, in a front-rear direction, through the arc guide rail 11 and the arc slide unit 12 in order to confirm and identify a pin tip of the positioning pin is located at an outer side of a middle of pedicle (namely the nailing point), where the tool sleeve 135 is adjusted to a predetermined depth (such as 105 mm).

(2) The awl device 52: With adjusted depth of the tool sleeve 135 being kept fixed at 105 mm, the arc guide rail 11 and the tool sleeve 135 are adjusted to get as close to a normal cutting angle as possible and then, the awl device 52 is positioned into the tool sleeve 135 for awl of the cortical bone of the patient to a depth of around 5 mm-10 mm.

(3) The puncture device 53: Afterwards, the puncture device 53 is placed into the tool sleeve 135 to reach the awl site and the threading fasteners 134 are rotated loosening to allow the surgeon to carry out puncture of pedicle by using a hammer or bare hands to apply a force to push the puncture device 53 into the interior of the middle of the pedicle to around 30 mm, and under this condition, identification of position can be further carried out with the arc guide rail 11 and the arc slide unit 12. Before the puncture device 53 is removed, the threading fasteners 134 are tightened first and thus, the direction of trace of the pedicle screw can be identified.

(4) The probe device 54: To further identify if the direction of trace is completely located inside the pedicle, the probe device 54 is used to inspect if the surrounding is completely bone.

(5) The tapping device 55: Use is made according the need of the surgery. To ensure better safety and smoothness of the operation of nailing, before the insertion of the pedicle screw, tapping can be made first with the tapping device 55.

In summary, the present invention provides a spinal fixation aiming apparatus that could effectively fix the drawbacks of the prior art. To use, the extendible/retractable bar is attached to an operation table and adjustment is made with the first adjustment unit, the second adjustment unit, and the extendible/retractable bar for setting a position of the spinal fixation aiming device to an angle and a height according to the patient. Further, according to the need of the surgical operation, a collaborative operation of the arc guide rail and the arc slide unit can be conducted for angular adjustment so that the tool holder can keep corresponding to a spinal fixation nailing site of the patient for any angle thereby providing an effect of easy operation and accurate aiming.

It will be understood that each of the elements described above, or two or more together may also find a useful application in other types of methods differing from the type described above.

While certain novel features of this invention have been shown and described and are pointed out in the annexed claim, it is not intended to be limited to the details above, since it will be understood that various omissions, modifications, substitutions and changes in the forms and details of the device illustrated and in its operation can be made by those skilled in the art without departing in any way from the claims of the present invention.

I claim:

1. A spinal fixation aiming apparatus, comprising:
a spinal fixation aiming device, which comprises an arc guide rail, an arc slide unit that is movably coupled to the arc guide rail, and a tool holder that is mounted to the arc slide unit, two ends of the arc guide rail being each formed with a mounting hole, the tool holder being movable to and selectively fixed at a predetermined location, wherein the arc guide rail, the arc slide unit, and the tool holder are each formed of a light-transmitting material;
a first adjustment unit, which is coupled to one of the mounting holes of the arc guide rail for adjusting inclination and height of the spinal fixation aiming device;
a second adjustment unit, which is coupled to the first adjustment unit for adjustably setting the spinal fixation aiming device to a first horizontal position or a second horizontal position; and
an extendible/retractable bar, which is movably coupled to the second adjustment unit for adjusting a height of the spinal fixation aiming device;
wherein the arc guide rail and the arc slide unit together form a spherical surface that define two separate arcs of the spherical surface such that the arc slide unit and the tool holder are able to slide along a spherical arc surface of the arc slide unit.

2. The spinal fixation aiming apparatus according to claim 1, wherein the arc slide unit comprises a base, guide sections respectively extending from ends of the base, through openings respectively formed in the guide sections and movably coupled to the arc guide rail, and a fixing knob selectively fixing the arc guide rail.

3. The spinal fixation aiming apparatus according to claim 2, wherein the tool holder comprises a coupling section, slide covers respectively arranged at two sides of the coupling section and respectively engageable with and coupled to the guide sections, an internally threaded section extending through each of the slide covers, and a threading fastener coupled to each of the internally threaded sections.

4. The spinal fixation aiming apparatus according to claim 1, wherein the tool holder receives a tool sleeve to position therein.

5. The spinal fixation aiming apparatus according to claim 1, wherein the first adjustment unit comprises a mounting section coupled to the second adjustment unit, an angle adjustment seat movably coupled to the mounting section, and a height adjustment seat movably coupled to the angle adjustment seat.

6. The spinal fixation aiming apparatus according to claim 5, wherein the angle adjustment seat is coupled to the mounting section by at least one first adjustment knob and the height adjustment seat is coupled to the angle adjustment seat by at least one second adjustment knob.

7. The spinal fixation aiming apparatus according to claim 1, wherein the second adjustment unit comprises a first rail movably coupled to the first adjustment unit, an adjustment fixer movably coupled to the first rail, and a second rail movably coupled with the extendible/retractable bar and the adjustment fixer.

8. The spinal fixation aiming apparatus according to claim 7, wherein each of the first rail and the second rail has one side that is provided with a toothed section.

9. The spinal fixation aiming apparatus according to claim 7, wherein the adjustment fixer comprises a first coupling section fit over and coupled to the first rail, a first fixing member mounted to one side of the first coupling section, a second coupling section fit over and coupled to the second rail, and a second fixing member mounted to one side of the second coupling section.

10. The spinal fixation aiming apparatus according to claim 9, wherein the first fixing member is set, in a releasable manner, in engagement with the toothed section of the first rail and the second fixing member is set, in a releasable manner, in engagement with the toothed section of the second rail.

11. The spinal fixation aiming apparatus according to claim 1, wherein the extendible/retractable bar has one end that is provided with a pivotal joint section that is movably coupled to the second adjustment unit and the pivotal joint section is provided, on one side thereof, with a pivot fastener.

\* \* \* \* \*